United States Patent [19]
Lynch et al.

[11] Patent Number: 6,153,384
[45] Date of Patent: Nov. 28, 2000

[54] HIGH THROUGHPUT SCREENING ASSAYS FOR NUCLEIC ACID LIGASE MODULATORS

[75] Inventors: Anthony Simon Lynch, Pacifica; Ashok Ramesh Sanadi, Sunnyvale; Mohanram Sivaraja, Palo Alto, all of Calif.

[73] Assignee: Tularik Inc., South San Francisco, Calif.

[21] Appl. No.: 09/025,979

[22] Filed: Feb. 19, 1998

[51] Int. Cl.[7] ............................... C12Q 1/68; C12P 19/34
[52] U.S. Cl. ............................ 435/6; 435/91.1; 435/91.2
[58] Field of Search ............................... 435/6, 91.1, 91.2

[56] References Cited

U.S. PATENT DOCUMENTS 5,705,344  1/1998  Giordano et al. ........................... 435/6

OTHER PUBLICATIONS

Jung et al, Ultrasensitive Instrumentation for DNA Sequencing and Biochemical Diagnostics,*Progress in Biomedical Optics*, 2386:118–127 (1995).
Automated Column Equilbration, Washing, Sample Loading and Elution of Bench–Packed Mini–Columns, *BioFeedback*, 12:(3) 336–338.
Samiotaki et al., Dual Color Ligation Assay, 239–242.
Weiss et al., "Enzymatic Breakage and Joining of Deoxyribonucleic Acid", *The Journal of Biological Chemistry* 243:17 4543–4555 (1968).
Institoris et al., "Benzamide Potentiation of the Cytotoxicity of Bifunctional Galacticol in Resistant P388 Leukemia Correlates With Inhibition of DNA Ligase II", *Cancer Chemother Pharmacol* 30: 325–329 (1992).
Wang et al., "Western Blots from Sodium Dodecyl Sulfate–Polyacrylamide Gels Stained by Metal Salts", *Analytical Biochemistry* 180: 311–313 (1989).
Tan et al., "Natural–Product Inhibitors of Human DNA Ligase I", *Biochem. J.*, 314: 993–1000 (1996).
Stewart Shuman, "Vaccinia Virus DNA Ligase: Specificity, Fidelity, and Inhibition", *Biochemistry* 34: 16138–16147 (1995).
Moore et al., "Purification and Electrophoretic Assay of T4–Induced Polynucleotide Ligase for the In Vitro Construction of Recombinant DNA Molecules", *Analytical Biochemistry* 75: 545–554 (1976).
John D. Karkas, "A New Method of Assay for Polynucleotide Ligase", *Biochimica et Biophysica Acta* 340 452–462 (1974).
Montccucco et al., "DNA Unwinding and Inhibition of T4 DNA Ligase by Anthracyclines", *Nucleic Acids Research* 16: 3907–3919 (1988).
Moore et al., Inhibition of Two Enzymes in De Novo Purine Nucleotide Synthesis by Triciribine Phosphate (TCN–P)*, *Biochemical Pharmacology*, 38:22 4045–4051 (1989).

*Primary Examiner*—Kenneth R. Horlick
*Assistant Examiner*—Jeffrey Siew
*Attorney, Agent, or Firm*—Townsend and Townsend and Crew LLP

[57] ABSTRACT

Screening assays for identifying ligase activity modulators are provided, in both solid phase and liquid phase formats. Solid phase formats detect ligase activity by ligating a labelled nucleic acid to a capture nucleic acid in the presence of the ligase modulator and detection of the labelled nucleic acid. Liquid phase assays detect ligation-dependent changes in interactive labels between nucleic acids such as proximity quenching of fluorescent labels. Compositions, apparatus and integrated systems for assays are also provided.

47 Claims, 8 Drawing Sheets

- HOMOGENOUS TIME RESOLVED FLUORESCENCE ENERGY TRANSFER ASSAY

- SUBSTRATES: OLIGONUCLEOTIDES CONTAINING SPECIFIC LABELS

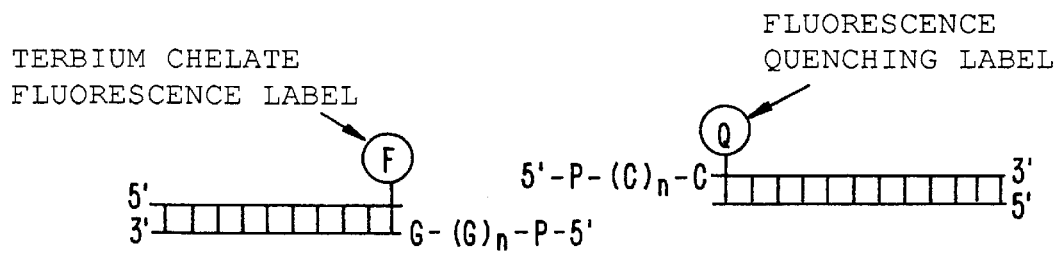

- REACTION: PERFORMED USING CONDITIONS WHEREIN THE FLUORESCENCE OF THE TERBIUM LABEL WILL ONLY BE EFFECTIVELY QUENCHED FOLLOWING LIGATION OF SUBSTRATES.

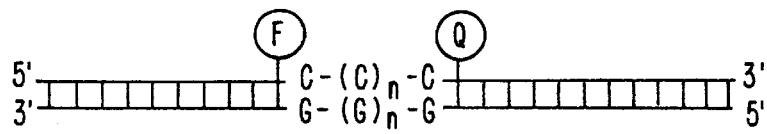

FOR EXAMPLE:

IF Q = TETRAMETHYLRHODAMINE THEN QUENCHING OF TERBIUM FLUORESCENCE IS OBSERVED UP TO 10 NM (29 BP) AWAY.

IF Q = A NITROXIDE SPIN LABEL THEN EFFECTIVE QUENCHING OF TERBIUM FLUORESCENCE IS ONLY OBSERVED UP TO 2 NM (6 BP) AWAY.

*FIG. 3.*

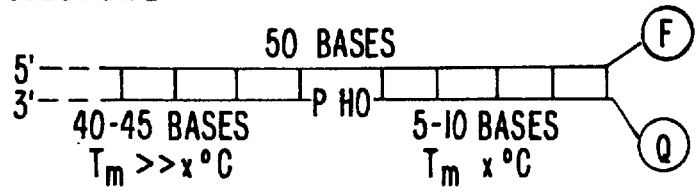
SUBSTRATE:
FOR EXAMPLE:
| | F LABEL | Q LABEL |
|---|---|---|
| WALLAC: | TERBIUM CHELATE | TRITC |
| PACKARD: | EUROPIUM CRYPTATE | ALLOPHYCOCYANIN |
MIX → REACT → HEAT TO $x^+$ C → MEASURE
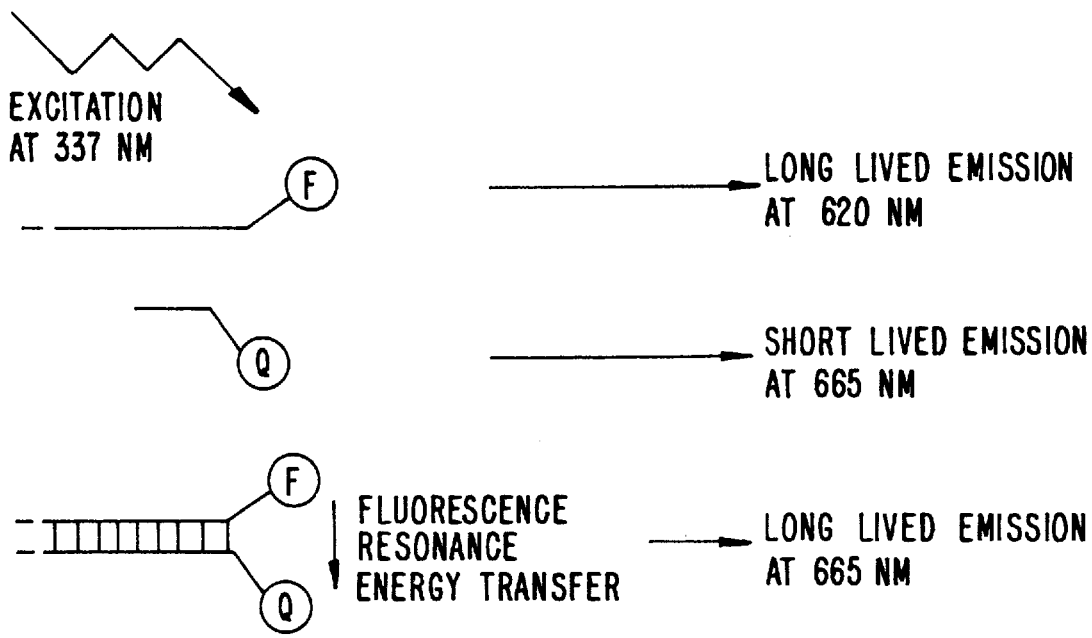
FIG. 4.

| Robotic Assay Data: Plate 1 | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 1216 | 10707 | 11363 | 11021 | 11336 | 8530 | 10839 | 15296 | 13263 | 12258 | 12949 | 13466 |
| B | 1009 | 12240 | 11793 | 10359 | 12456 | 8128 | 10827 | 11930 | 16430 | 11662 | 11085 | 14378 |
| C | 1000 | 11305 | 14879 | 13890 | 11933 | 11555 | 13314 | 13579 | 13121 | 11462 | 10218 | 14383 |
| D | 1177 | 13810 | 14114 | 12947 | 12068 | 16434 | 13549 | 13218 | 13070 | 11844 | 12797 | 13070 |
| E | 878.2 | 13667 | 11724 | 12865 | 12020 | 13519 | 12452 | 14390 | 12115 | 12267 | 10636 | 11539 |
| F | 1032 | 19131 | 15457 | 11814 | 14760 | 14515 | 14260 | 15031 | 14594 | 19022 | 10263 | 12463 |
| G | 856 | 15239 | 20691 | 14220 | 15111 | 10072 | 10903 | 12640 | 14009 | 17949 | 10210 | 13216 |
| H | 914.4 | 10950 | 10471 | 12043 | 10100 | 8694 | 14278 | 12370 | 11215 | 13559 | 14430 | 13967 |

| Robotic Assay Data: Plate 2 | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 938.7 | 17141 | 19368 | 17424 | 11346 | 13379 | 13904 | 10147 | 14106 | 11197 | 13686 | 13676 |
| B | 800.8 | 11940 | 16029 | 13582 | 15603 | 3344 | 12247 | 13377 | 15646 | 10028 | 16716 | 16081 |
| C | 839 | 17628 | 11345 | 19057 | 14170 | 12713 | 14707 | 14407 | 15987 | 12575 | 14247 | 15051 |
| D | 1255 | 13456 | 17945 | 19210 | 14826 | 14926 | 19833 | 11882 | 17368 | 12096 | 10259 | 15733 |
| E | 811.4 | 15585 | 12914 | 12914 | 13169 | 16310 | 11548 | 14269 | 12425 | 15464 | 14464 | 15390 |
| F | 896 | 17264 | 18000 | 13529 | 20308 | 12865 | 16052 | 12245 | 14667 | 20970 | 11554 | 14555 |
| G | 782 | 17441 | 16235 | 12525 | 13404 | 10778 | 17008 | 8202 | 17387 | 14020 | 10737 | 15466 |
| H | 898 | 14353 | 10452 | 13043 | 11366 | 11867 | 22830 | 14691 | 11327 | 10030 | 13376 | 17708 |

| Robotic Assay Data: Plate 3 | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 854.5 | 15760 | 16449 | 14160 | 11513 | 12458 | 9784 | 11531 | 10019 | 10464 | 11944 | 12554 |
| B | 818.4 | 13765 | 11776 | 11675 | 10187 | 11264 | 10147 | 12548 | 9637 | 10227 | 11064 | 12760 |
| C | 767.3 | 14335 | 13687 | 12059 | 12505 | 11376 | 12889 | 11172 | 11104 | 9925 | 12308 | 12549 |
| D | 668.1 | 11131 | 12013 | 13289 | 13006 | 12953 | 12385 | 11850 | 10043 | 11080 | 10695 | 12449 |
| E | 665.2 | 12599 | 12752 | 12451 | 13632 | 12607 | 12718 | 13621 | 12154 | 12141 | 11869 | 12846 |
| F | 650.2 | 15319 | 14954 | 14797 | 14444 | 14752 | 15030 | 14307 | 13486 | 13450 | 11695 | 12547 |
| G | 627.8 | 15464 | 16442 | 15256 | 13245 | 12302 | 13848 | 13839 | 13387 | 13046 | 13390 | 12852 |
| H | 725.4 | 11836 | 18397 | 20641 | 15963 | 13593 | 13398 | 10730 | 14115 | 12557 | 13390 | 14489 |

| Robotic Assay Data: Plate 4 | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 857.5 | 18847 | 17680 | 13654 | 12211 | 15008 | 12401 | 11612 | 10000 | 12148 | 14259 | 11141 |
| B | 632.5 | 12846 | 10943 | 14113 | 12904 | 11132 | 12185 | 11801 | 13842 | 11828 | 12680 | 11784 |
| C | 613.8 | 12373 | 14407 | 11478 | 13574 | 11390 | 11752 | 11663 | 11845 | 11576 | 11132 | 13504 |
| D | 606 | 10577 | 11868 | 14759 | 10671 | 11265 | 11220 | 11826 | 11376 | 11987 | 11070 | 13956 |
| E | 590.3 | 10052 | 11496 | 10755 | 11505 | 10337 | 12187 | 11172 | 11033 | 10180 | 11319 | 13816 |
| F | 581.6 | 8336 | 13390 | 13537 | 14547 | 13862 | 11109 | 11804 | 11858 | 11645 | 13399 | 13644 |
| G | 614.9 | 11353 | 13922 | 14934 | 14094 | 13299 | 13205 | 14184 | 16386 | 15571 | 15270 | 12613 |
| H | 667 | 11026 | 13651 | 16262 | 18806 | 17803 | 16432 | 16619 | 15808 | 15673 | 14299 | 13141 |

FIG. 7.

HIGH THROUGHPUT SCREENING ASSAYS FOR NUCLEIC ACID LIGASE MODULATORS

FIELD OF THE INVENTION

The field of the invention relates to high-throughput assays for identifying modulators of ligase activity. New solid and liquid phase assays are described, as are related compositions, apparatus and integrated systems.

BACKGROUND OF THE INVENTION

Polynucleotide ligases are enzymes which create a covalent bond between discontinuous nucleic acids. This joining of discontinuous nucleic acids by polynucleotide ligases plays a central role in a number of natural biological processes, including chromosome replication, genetic recombination and cellular repair of environmental genetic damage (e.g., X-ray damage). Polynucleotide ligases from virues, prokaryotic cells and eukaryotic cells have been described and characterized. In particular, $NAD^{30}$-dependent nucleic acid ligases of the eubacteria and the ATP-dependent nucleic acid ligases of eukaryotes are well characterized and serve essential functions in such cells.

Compounds which modulate ligase activity can act as cytotoxic agents by disrupting cellular processes in normal cell division processes. Modulators with adequate specificity can serve as antibacterial, antifungal, or antineoplastic agents. Similarly, as polynucleotide ligases are also virally encoded (or, in some cases, induced by viral infection), modulators of viral ligase activity can act as antiviral agents.

In addition to the role of polynucleotide ligases in biology and medicine, the ligation of polymerized nucleic acids is a necessary step in the fundamental techniques of molecular biology. Ligation of DNA and RNA polymers is ubiquitous in the common techniques of cloning, sequencing and analyzing genetic material. There are several general texts which describe ligation generally in recombinant techniques, such as Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1997) ("Ausubel"). Similarly, techniques utilizing ligation are becoming increasingly important as general tools of basic research and in diagnostic clinical settings. The ligation chain reaction ("LCR"; sometimes denoted the "ligation amplification reaction" or "LAR") and related techniques are of increasing utility, particularly as diagnostic tools.

Given the many roles for ligase enzymes, ligase modulators which increase or decrease ligase activity, or which increase or decrease ligase specificity, would be useful in medicine, biology, or as general laboratory tools. Accordingly, various assays to identify compounds which affect ligase activity have been performed. For example, Tan et al. (1996) *Biochem J*. 314:993–1000 describe screening of potential inhibitors of human DNA ligase I (hLI) by mixing ligase reactants and plant extracts in microtiter dishes, followed by spotting the resulting products onto filter paper and scintillation counting.

Improved high-throughput assays which identify nucleic acid ligase modulators are, therefore, desirable. The present invention provides such high-throughput assays, as well as other features which will become apparent upon review.

SUMMARY OF THE INVENTION

High throuput assays for screening of nucleic acid ligase modulators are provided. Inhibitors and activators of ligase activity can both be screened using the assays, as can modulators which alter the substrate specificity of ligases. Solid and liquid phase high throughput assays are provided, as are related assay compositions, integrated systems for assay screening and other features which will be evident upon review.

In one aspect, high-throughput solid phase assays are provided. In solid phase formats, a first nucleic acid is fixed (covalently or non-covalently) to a solid support. A second nucleic acid having a label is ligated to the first nucleic acid with a nucleic acid ligase, and the amount of label fixed to the solid support by the action of the ligase is determined. The addition of a modulator to the ligation mixture inhibits or facilitates the action of the nucleic acid ligase, increasing or decreasing the amount of label bound to the solid support.

In a second aspect, high-throughput liquid phase assays are provided. In these assays, a first nucleic acid is ligated to a second nucleic acid in a fluidic sample (e.g., an aqueous ligation mixture in a well on a microtiter dish). The first nucleic acid has a first label, and the second nucleic acid has a second label. When the first and second labels are brought into proximity in the liquid phase, the detectable emission of the first or second label (or both labels) changes. Ligation of the first and second nucleic acid brings the labels into proximity, thereby affecting the emission characteristics of the first or second label. Nucleic acid ligase activity is determined by measuring label emissions and changes in label emissions. In these assays, a modulator causes a change in nucleic acid ligase activity, resulting in a detectable change in label emissions, or in the rate of change from one label emission to another. Example labels which change emission characteristics upon proximity to a second label include fluorescent labels and calorimetric labels.

Kits, compositions and integrated systems for performing the assays are also provided.

BRIEF DESCRIPTION OF THE DRAWING

FIG. 3 is a drawing of a first time resolved fluorescence assay utilizing quenching labels.

FIG. 4 is a drawing of a second time resolved fluorescence assay utilizing quenching labels.

FIG. 7 is a data set for a representative robotic assay format.

DETAILED DESCRIPTION OF THE INVENTION

Figure 1:
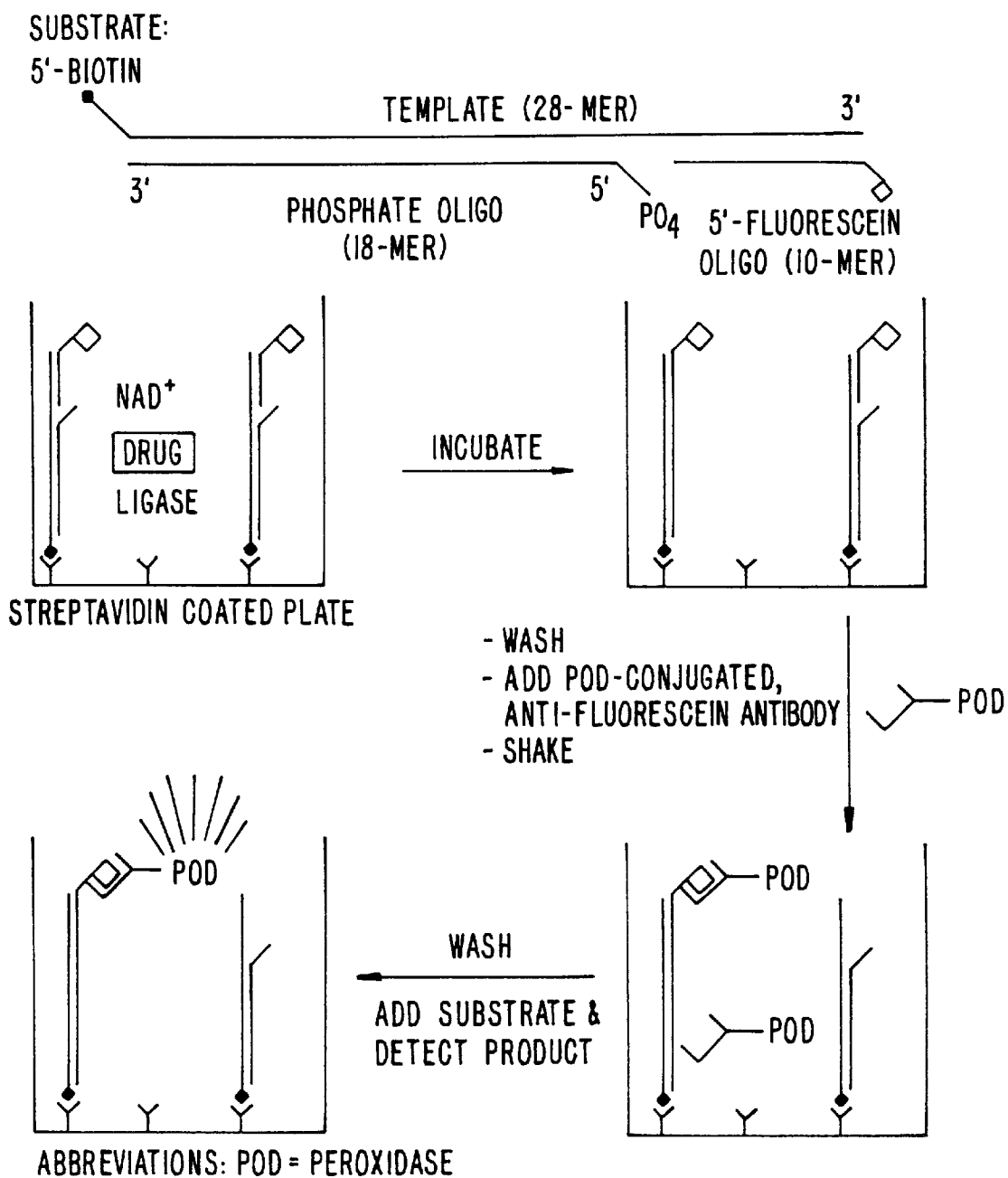
FIG. 1 is a drawing of a solid phase assay of the invention utilizing a POD-conjugated anti-fluorescein antibody.

High-throughput methods, compositions, kits and integrated systems for detecting ligation activity and the effect of potential modulators of this activity are provided. These modulators have value for in vitro modification of nucleic acid ligase activity, e.g., as tools for recombinant methods, cell culture modulators, or the like. More importantly, these modulators provide lead compounds for drug development for a variety of conditions, including antibacterial, anlifungal, antiviral or antineoplastic agents. Accordingly, the assays are of immediate value for their ability to identify lead compounds for pharmaceutical or other applications.

Indeed, because ligases are important in a variety of biological processes relating to cell division, replication, repair and infection, modulators identified by the assays of the invention are leads for a variety of conditions, including neoplasia, inflammation, allergic hypersensitivity, metabolic disease, genetic disease, viral infection, bacterial infection, fungal infection, or the like. In addition, ligase modulators which specifically target undesired organisms, such as viruses, fungi, agricultural pests, or the like, can serve as fungicides, bactericides, herbicides, insecticides, etc. Thus, the range of conditions that ligase activity modulators are applicable to includes conditions in humans and other animals, and in plants, e.g., for agricultural applications.

The invention represents an improvement over existing technology in several ways. For example, (a) there is no requirement that radioactive reagents be employed (although they are optionally used as discussed below); (b) there is no requirement that additional enzymatic components in the assay be provided as is common to bench-top assays (certain immune detection reagents are preferred as described below, but not necessary for practicing the invention); (c) assays can be performed in the liquid or solid-phase; (d) through utilization of different combinations of oligonucleotides, the assay can readily be adapted to screen for ligation of many different types of substrates including those of specific DNA or RNA sequences; (e) any of the formats described, including the liquid phase time resolved format ("TRF") is readily amenable for automation and high throughput screening ("HTS") using current reagents, devices and methodologies.

Further in this regard, several aspects of the discovery were surprising. First, the assay can be performed in a very short time frame relative to other polynucleotide assay formats; for $E.$ $coli$ $NAD^{30}$-dependent DNA ligase using the solid-phase format, the whole assay can be performed in under two hours (with an enzymatic reaction period of 30 mins at 22° C.). For the homogenous TRF assay, the complete assay is as short as one hour. Second, the assay is extremely sensitive relative to previously described formats and requires only minimal quantities of the necessary reagents. Typically, the ligase is employed in the 10–100 pM range; in cases where the availability of the polynucleotide ligase is limiting, this assay format has a significant advantage over other pervious assay formats. Third, because of the high sensitivity of the assays, it is very economical to run the assays in an automated high-throughput format; for the $E.$ $coli$ $NAD^{30}$-dependent DNA ligase assay using commercially available reagents at retail price, this costs roughly <$1,000 per 10,000 sample wells (assuming a reaction volume of 100 μL). Finally, the assays are very robust with insignificant variation seen between control reactions, minimizing the need for repetitive control and calibration steps.

Ligases useful in the assays of the present invention are derived from any of a variety of sources, with many ligases being commercially available. For example, four distinct ligases have been identified in mammalian cells. See, Tomkinson et al. (1991) *J. Biol. Chem.* 266:21728–21733; Lindahl and Barnes (1992) *Annu Rev. Biochem.* 61:251–281; and Wei et al. (1995) *Mol Cell Biol.* 15:3206–3216. A human cDNA encoding the 102 kDa DNA ligase I (hLI) has been cloned and sequenced. See, Barnes et al. (1990) *Proc. Natl. Acad. Sci. USA* 87:6679–6683. hLI has also been functionally expressed in yeast, providing a ready source of the enzyme. See, Barnes, id and Petrini (1991) *Proc. Natl. Acad. Sci. USA* 88:7615–7619. hLI is the major ligase present in proliferating human cells and also plays a role in constitutive excision-repair. See, Barnes, id and Tomkinon et al. (1991), supra. Human DNA ligases (hL) and inhibitors of hLI are described in Tan et al. (1996) *Biochem J.* 314: 993–1000 and the reference therein, as is a low-throughput assay for identifying inhibitors. Eukaryotic type II–IV ligases are also important for cellular proliferation and excision repair. See, e.g., Institoris et al. (1992) *Cancer Chemother Pharmacol.* 30:325–329. These ligases have been purified from a variety of sources. For example, DNA ligase II has been purified from calf thymus DNA. See, Terakoa et al. (1986) *J. Biol. Chem* 261:6888. Wei et al (1995), supra describe the isolation of a cDNA for DNA ligases III and IV.

In addition to eukaryotic sources for ligases, a variety of bacterial ligases are also currently available. Bacterial ligases are commercially available from a variety of sources known to one of skill. For example, *E. coli* DNA Ligase is available from New England Biolabs, as well as from a variety of other sources. *E. coli* DNA ligase serves as a model for other bacterial ligases and compounds which modulate *E. coli* ligase activity typically modulate the activity of other bacterial ligases as well, making it possible to use *E. coli* ligase in screens for antibacterial compounds. Modulators of *E coli* ligase are also useful as general laboratory tools, as *E. coli* and $T_4$ ligases are ubiquitous to molecular biology.

Viral ligases are also well-known and available. For example, ATP-dependent ligases from pox viruses were described by Kerr and Smith (1989) *Nuc Acids Res* 17:9039–9050; Colinas et al. (1990) *Virology* 179:267–275; Parks et al. (1994) *Virology* 202:642–650, and Skinner et al. (1994) *J. Gen Virol.* 75:2495–2498. ATP-dependent ligase from African Swine fever virus was described by Hammond et al. (1992). The pox-virus ligases are very closely related to the eukaryotic type II and III ligases (which are, themselves, very closely related). See, Shuman (1995) *Biochemistry* 34:16138–16147 and the references cited therein. Other viral ligases are also known and available.

In the assays of the invention, preferred ligases are selected from medically relevant sources such as human ligase I, II, III, or IV (e.g., for assays designed to identify compounds which modulate cell growth, e.g., for inhibition of neoplasia); or from infectious organisms such as infectious fungi, e.g., Aspergillus, Candida species; bacteria, particularly *E. coli*, which serves a model for pathogenic lacteria, as well as medically important bacteria such as Staphylococci (e.g *aureus*), Streptococci (e.g. *pneumoniae*), Clostridia (e.g. *perfringens*), Neisseria (e.g *gonorrhoea*), Enterobacteriaceae (e.g. *coli*), Helicobacter (e.g *pylori*), Vibrio (e.g. *cholerae*), Capylobacter (e.g. *jejuni*), Pseudomonas (e.g *aeruginosa*), Haemophilus (e.g. *influenzae*), Bordetella (e.g. *pertussis*), Mycoplasma (e.g. *pneumoniae*), Ureaplasma (e.g. *urealyticum*), Legionella (e.g. *pneumophila*), Spirochetes (e.g. Treponema, Leptospira and Borrelia), Mycobacteria (e.g. *tuberculosis, smegmatis*), Actinomyces (e.g. (*israelii*), Nocardia (e.g. *asteroides*), Chlamydia (e.g. *trachomatis*), Rickettsia, Coxiella, Ehrilichia, Rochalimaea, Brucella, Yersinia, Fracisella, and Pasteurella; protozoa such as sporozoa (e.g. Plasmodia), rhizopods (e.g. Entamoeba) and flagellates (Trypanosoma, Leishmania, Trichomonas Giardia, etc.); viruses such as (+) RNA viruses (examples include Poxviruses e.g., *vaccinia*, Picornaviruses, e.g. *polio*; Togaviruses, e.g. rubella; Flaviviruses, e.g. HCV; and Coronaviruses), (−) RNA viruses (examples include Rhabdoviruses, e.g. VSV; Paramyxovimses, e.g. RSV; Orthomyxovimses, e.g. influenza; Bunyaviruses and Arenaviruses), dsDNA viruses (Reoviruses, for example), RNA to DNA viruses, i.e. Retroviruses, e.g. HIV and HTLV, and certain DNA to RNA viruses such as Hepatitis B virus. Other assays are designed to be relevant to non-medical uses, such as assays for inhibitors of ligases from crop pests e.g., insects, fungi, weed plants, and the like. Preferred ligases include $NAD^{30}$ dependent ligases (ligases which have elevated activity levels in the presence of $NAD^{30}$ or an $NAD^{30}$ analogue) and ATP-dependent ligases (ligases which have elevated activity levels in the presence of ATP or an ATP analogue).

Nucleic acid ligases may be purified from a natural source or may be recombinant and are usually provided in at least a partially-purified form. Occasionally only a portion of a native ligase is used in the assay, the portion being sufficient for ligase activity of preferably not less than an order of magnitude less than that of the full-length ligase. Portions capable of imparting the requisite binding specificity and affinity are readily identified by those skilled in the art and may be fused via recombinant DNA methods to peptide sequences which facilitate affinity purification of the resulting fusion protein which retains nucleic acid ligase activity (e.g., a polyhistadine tag). A wide variety of molecular and biochemical methods are available for generating catalytic fragments of a nucleic acid ligase. Examples of appropriate molecular techniques for generating recombinant portions of a protein, and instructions sufficient to direct persons of skill through many cloning exercises are found in Berger and Kimmel, *Guide to Molecular Cloning Techniqiues, Methods in Enzymolog volume* 152 Academic Press, Inc., San Diego, Calif. (Berger); Sambrook and Ausubel (both supra). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochernika Analytika (Fluka Chemie AG, Buchs, Switzerland), Invitrogen, San Diego, Calif., and Applied Biosystems (Foster City, Calif.), as well as many other commercial sources known to one of skill.

In the assays of the invention, ligases are used to ligate nucleic acids. Most commonly, these nucleic acids are oligonucleotides which are made synthetically. Synthetic oligonucleotides are typically synthesized chemically according to common solid phase phosphoramidite triester methods described, e.g., by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Oligonucleotides can also be custom made and ordered from a variety of commercial sources known to persons of skill. In other embodiments, the nucleic acids are made recombinantly according to standard techniques, described, e.g., in Berger, Sambrook and Ausubel, supra.

As noted, the invention provides both solid phase and liquid phase assays in high throughput format. In either format, the assays include incubation of a ligase and appropriate ligatable nucleic acids in the presence of a ligase activity modulator. The assays of the invention provide for highly uniform screening of modulators in either the liquid or solid phase. Accordingly, control reactions which measure the activity level of the ligase in a ligation mixture which does not include a ligase modulator are generally unnecessary. However, such optional control reactions are appropriate and increase the reliability of the assay. Accordingly, in a preferred embodiment, the methods of the invention include such a control reaction.

Solid Phase Assays

In the solid phase assays of the invention, an effect of a potential ligase activity modulator on the activity of a nucleic acid ligase is determined. In the assays, a test ligation mixture which includes the nucleic acid ligase, a tagged nucleic acid comprising a tag, a labeling nucleic acid comprising a primary label, and a potential activity modulator are incubated. The tag is bound to a solid support, thereby binding the tagged nucleic acid to the solid support. The extent of ligation of the labeling nucleic acid to the tagged nucleic acid is then determined by measuring the amount of label ligated to the tagged nucleic acid by ligating the labeling nucleic acid to the tagged nucleic acid.

Ligases

As discussed above, a variety of ligases can be used in the ligation mixture, with the selection being determined by the intended application. For example, where the assay is used to screen for anti-neoplastic ligase modulators, a eukaryotic ligase such as hLI is used in the assay. Similarly, where the assays is designed to screen for an antibacterial ligase modulator, a bacterial ligase such as *E. coli* ligase is used. Any of the ligases described supra can be used in the solid or liquid phase assays. In one aspect, ligases are differentially screened to identify modulators which modulate the activity of a first ligase, but do not modulate the activity of a second ligase. For example, where a bacterial ligase modulator is desired, both a bacterial and a eukaryotic ligase can be screened (simultaneously, in a serial or parallel format, or separately) to identify modulators which modulate the activity of the bacterial ligase, but which do not modulate the activity of the eukaryotic ligase.

Molecular Tags and Solid Substrates

The tag can be any of a variety of components. In general, a molecule which binds the tag (a tag binder) is fixed to a solid support, and the tagged DNA is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fe region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. See, id. Indeed, the antibody can be either the tag or the tag binder, or antibodies can be used as both tags and tag binders. For example, in one common configuration, the tag is a first antibody and the tag binder is a second antibody which recognizes the first antibody. In addition to antibody-antigen interactions, receptor-ligand interactions are also appropriate as tall and tag-binder pairs. For example, agonists and antagonists of cell membrane receptors (e.g., cell receptor-ligand interactions such as e.g., transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook* Academic Press New York and Hulme (ed) *Receptor Ligand Interactions A Practical Approach* Rickwood and Hames (series editors) Hulme (ed) IRL Press at Oxford Press N.Y.).

Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Specific tag-tag binder interactions occur when the tag and tag binder bind with a $K_D$ of at least about 0.01 $\mu$M, preferably at least about 0.001 $\mu$M or better, and most typically and preferably, 0.0001 $\mu$M or better, under standard assay conditions.

Synthetic attachment of DNA or RNA nucleic acids to various appropriate tags is performed using available techniques. In one embodiment, linkers are added to the nucleic acid and attachment to the tag is performed through the linker. Common linkers include polypeptide sequences, such as poly gly sequences of between about 5 and 200 amino acids. In some embodiments, proline residues are incorporated into the linker to prevent the formation of significant secondary structural elements by the linker. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivitized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes, and hydroxyalkylsilanes can be used to functionalize a variety of surfaces, such as glass surfaces. The construction of such solid phase biopolymer arrays is well described in the literature. See, e.g., Merrifield (1963) J. Am. Chem. Soc. 85: 2149–2154 (describing solid phase synthesis of, e.g., peptides); Geysen et al. (1987) J. Immun. Meth. 102: 259–274 (describing synthesis of solid phase components on pins). See, Frank and Doring (1988) Tetrahedron 44: 6031–6040 (Describing synthesis of various peptide sequences on cellulose disks); Fodor et al. (1991) *Science*, 251: 767–777; Sheldon et al. (1993) Clinical Chemistry 39(4): 718–719 and Kozal et al. (1996) *Nature Medicine* 2(7): 753–759 (all describing arrays of biopolymers fixed to solid substrates). Non-chemical approaches for fixing tag binders to substrates include other common methods, such as heat, cross-linking by UV radiation, and the like.

Similarly, the tagged nucleic acid may be directly attached to a solid substrate in the assays of the invention. In this embodiment, the terminal end of the tagged nucleic acid is, itself, the molecular tag. In this embodiment, tagged nucleic acids are fixed to or synthesized on a solid support. A solid support is a matrix of material in a substantially fixed arrangement. Exemplar solid supports include glasses, plastics, polymers, metals, metalloids, ceramics, organics, etc. For example, using chip masking technologies and photoprotective chemistry it is possible to generate arrays of nucleic acid probes. These arrays, which are known, e.g., as "DNA chips," can include millions of nucleic acid regions on a substrate having an area of about 1 cm$^2$ to several cm$^2$, thereby incorporating sets of from a few to millions of tagged nucleic acids. See, e.g., Fodor et al. (1991) *Science*, 251: 767–777; Sheldon et al. (1993) Clinical Chemistry 39(4): 718–719, and Kozal et al. (1996) *Nature Medicine* 2(7): 753–759.

Labels

The labels in the present invention can be primary labels (where the label comprises an element which is detected directly) or secondary labels (where the detected label binds to a primary label, e.g., as is common in immunological labeling). An introduction to labels, labeling procedures and detection of labels is found in Polak and Van Noorden (1997) *Introduction to Immunocytochemistry* second edition, Springer Verlag, N.Y. and in Haugland (1996) *Handbook of Fluorescent Probes and Research Chemicals* a combined handbook and catalogue Published by Moltecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodintine isothiocynate (TRITC), etc.), dixogenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) spectral calorimetric labels such as colloidal gold or colored glass or plastic (e.g. polystyrene, polypropylene, latex, etc.) beads. The label may be coupled directly or indirectly to a component of the detection assay (e.g., the labeling nucleic acid) according to methods well known in the art. As indicated above, a wide variety of labels may be used, with the choice of label depending on sensitivity required, ease of conjugation with the compound, stability requirements, available instrumentation, and disposal provisions. In general, a detector which monitors a probe-target nucleic acid hybridization is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling nucleic acids is digitized for subsequent computer analysis.

Preferred labels include those which utilize 1) chemiluminescence (using Horseradish Peroxidase and/or Alkaline Phosphatase with substrates that produce photons as breakdown products) with kits being available, e.g., from Molecular Probes, Amersham, Boehringer-Mannheim, and Life Technologies/Gibco BRL; 2) color production [using both Horseradish Peroxidase and/or Alkaline Phosphatase with substrates that produce a colored precipitate] [kits available from Life Technologies/Gibco BRL, and Boehringer-Mannheim]; 3) hemifluorescence using, e.g., Alkaline Phosphatase and the substrate AttoPhos [Amersham] or other substrates that produce fluorescent products, 4) Fluorescence [e.g., using Cy-5 [Amersham], fluorescein, and other fluorescent tags]; 5) radioactivity using, kinase enzymes or other end-labeling approaches, nick translation, random priming, or PCR to incorporate radioactive molecules into the labeling nucleic acid. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

Most typically, ligation is measured by quantitating the amount of label fixed to the solid support by the action of a ligase enzyme. Typically, presence of a modulator in the ligation mixture will increase or decrease the amount of label fixed to the solid support relative to a control reaction which does not comprise the modulator, or as compared to a baseline established for a particular lot of ligase. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Nucleic Acid Configurations

As described supra, a wide variety of recombinant and synthetic techniques are available for making the tagged and labeling nucleic acids. The labeling and tagged nucleic acids can be any molecule ligatable by a nucleic acid ligase, including: a single-stranded RNA, a double-stranded RNA, a single-stranded DNA, a double-stranded DNA, a double-stranded DNA-RNA hybrid, an RNA analogue, and a DNA analogue. The tagged nucleic acid is covalently or non-covalently attached to a tag (including the case noted above in which the tag is simply a terminal nucleotide on the nucleic acid). The labeling nucleic acid is covalently or non-covalently attached to a primary label, which is optionally attached to a detectable secondary label.

It is a discovery of this invention that ligase enzymes typically need only small nucleic acid substrates for efficient ligation. For example, as long as the nucleic acid which acts as a phosphate donor strand in the ligation reaction is at least about 18 nucleotides and the phosphate acceptor strand is at least about 10 nucleotides in length, the ligase reaction proceeds efficiently. Accordingly, typical tagged nucleic acids will comprise at least about 15 nucleotides, generally at least about 18 nucletoides, generally 18–40 nucleotides, occasionally 18–50 nucleotides and occasionally more than 50 nucleotides. Typical labeling nucleic acids will comprise at least about 8 nucleotides, generally at least about 10 nucleotides, occasionally about 10–20 nucleotides, and occasionally more than 20 nucleotides. The tagged nucleic acid optionally has a template strand as well as a phosphate donor strand, where the template strand has a region complementary to the labeling nucleic acid to position the labeling nucleic acid in proximity to the phosphate donor strand. Accordingly, the template nucleic acid can be longer than the phosphate donor strand. Typical lengths for the template strand are longer than the phosphate donor strand by about the length of the labeling nucleic acid, although other arrangements are also appropriate (e.g. the template strand can overhang all or only a portion of the phosphate donor or phosphate acceptor strand). Thus, a typical template strand is about 28 nucleotides, but can be less or more, depending on the size of the region complementary to the phosphate donor strand, and the length of the region complementary to the labeling nucleic acid.

Short oligonucleotides (as opposed to longer nucleic acids) are preferred substrates for ligation because they can be made synthetically, because hybridization and washing in the assays leads to lower background levels and because they can be synthesized directly on the solid phase, if desired.

It is known that ligation reactions proceed more efficiently when the nucleic acids to be ligated have end regions which overlap (are single stranded and complementary), due to the increased proximity of the strands to be ligated. "Blunt ended" ligation also occurs at a measurable rate, and can be used in the assays of the intention.

In one embodiment, the tagged nucleic acid is partially double stranded, having a template strand and a phosphate donor strand having a terminal 5' phosphate. The template strand overhangs the phosphate donor strand, thereby providing a single-stranded template overhang. The labeling nucleic acid comprises a single stranded region complementary to the overhang. This arrangement of nucleic acids improves the efficiency of the ligation reaction for the reasons noted above.

Hybridization and Wash Strategies

In a preferred aspect, a labeling nucleic acid is hybridized to a tagged nucleic acid and the nucleic acids are ligated as described above. The resulting ligated nucleic acid is fixed to the solid support through a tag. Unligated labeling nucleic acid from the ligation reaction is typically then washed from the solid support using one or more washes, and, optionally, heat. An extensive guide to the hybridization and washing of nucleic acids is found in Tijssen (1993) *Laboratory Techniques in biochemistry and molecular biology—hybridization with nucleic acid probes parts I and II*, Elsevier, New York, and, Choo (ed) (1994) Methods In Molecular Biology Volume 33—*In Situ Hybridization Protocols* Humana Press Inc., New Jersey, as well as in Sambrook, Ausubel and Berger, supra.

It is expected that one of skill is fully capable of selecting appropriate hybridization conditions for the ligation reaction and appropriate wash buffers and conditions for removing unligated labeling nucleic acids from the solid substrate. In general, two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid.

Wash conditions are selected so that tags remain bound to any tag binders, and so that double-stranded ligated nucleic acids remain hybridized together. Typically, a low-stringency wash is adequate to remove unligated labeling nucleic acids. An example low stringency wash is 2×SSC at room temperature for 1–2 minutes. A higher stringency wash can also be used in some applications, e.g , a 0.2×SSC at 30–40° C. for 1–2 minutes (see, Sambrook, supra for a description of SSC buffer), or a wash using water at room temperature. Additional preferred wash conditions are described herein; moreover, such wash conditions are easily selected by one of skill, or determined by simple wash titration runs. In general, washes are repeated until a signal to noise ratio of 2×–10× (or higher) is achieved, i.e., until at least about 50–90% of the unligated nucleic acid is removed from the solid support, and often until at least 90–95% is removed. The d(termination of how much unligated labeling nucleic acid remains can be done by performing a calibration of the assay, by performing the ligation in the absence of a modulator and then repeatedly washing the solid support to determine the amount bound to the support through the tag, and the number of washes required to remove unbound labeling nucleic acid.

Model Solid Phase Assays

The solid phase assays of the invention are further illustrated by consideration of the attached figures. These assays are provided by way of illustration and not by way of limitation; one of skill will recognize a variety of substitutions that can be made upon complete review of this disclosure.

FIG. 1 depicts a preferred exemplar assay of the invention. A tagged DNA having a biotin tag and consisting of a template strand and a phosphate donor strand is fixed to a streptavidin or neutravidin coated plate by attachment through the biotin tag. A labeling DNA having a 5'-fluorescein label is incubated with the tagged DNA in the presence of a nucleic acid ligase and appropriate co-factors (e.g., $NAD^{30}$ or ATP) in a ligation mixture. The labeling DNA is complementary to a portion of the template strand and hybridizes to the template strand, placing the labeling DNA in proximity to the phosphate donor strand. The nucleic acid ligase catalyzes chemical ligation of the labeling strand to the phosphate donor strand. Following ligation of the labeling DNA and capture of the biotin tag, the any unligated labeling DNA is washed from the solid support. Ligation is detected by detecting the amount of label bound to the solid support. Changes in ligation due to the addition of a ligase modulator ("DRUG" in the FIG. 1) to the ligation mixture are measured by measuring the resulting difference in the amount of label bound to the solid support. In the depicted assay, the detected label is a an anti-fluorescein antibody having an enzymatic label.

Figure 2:
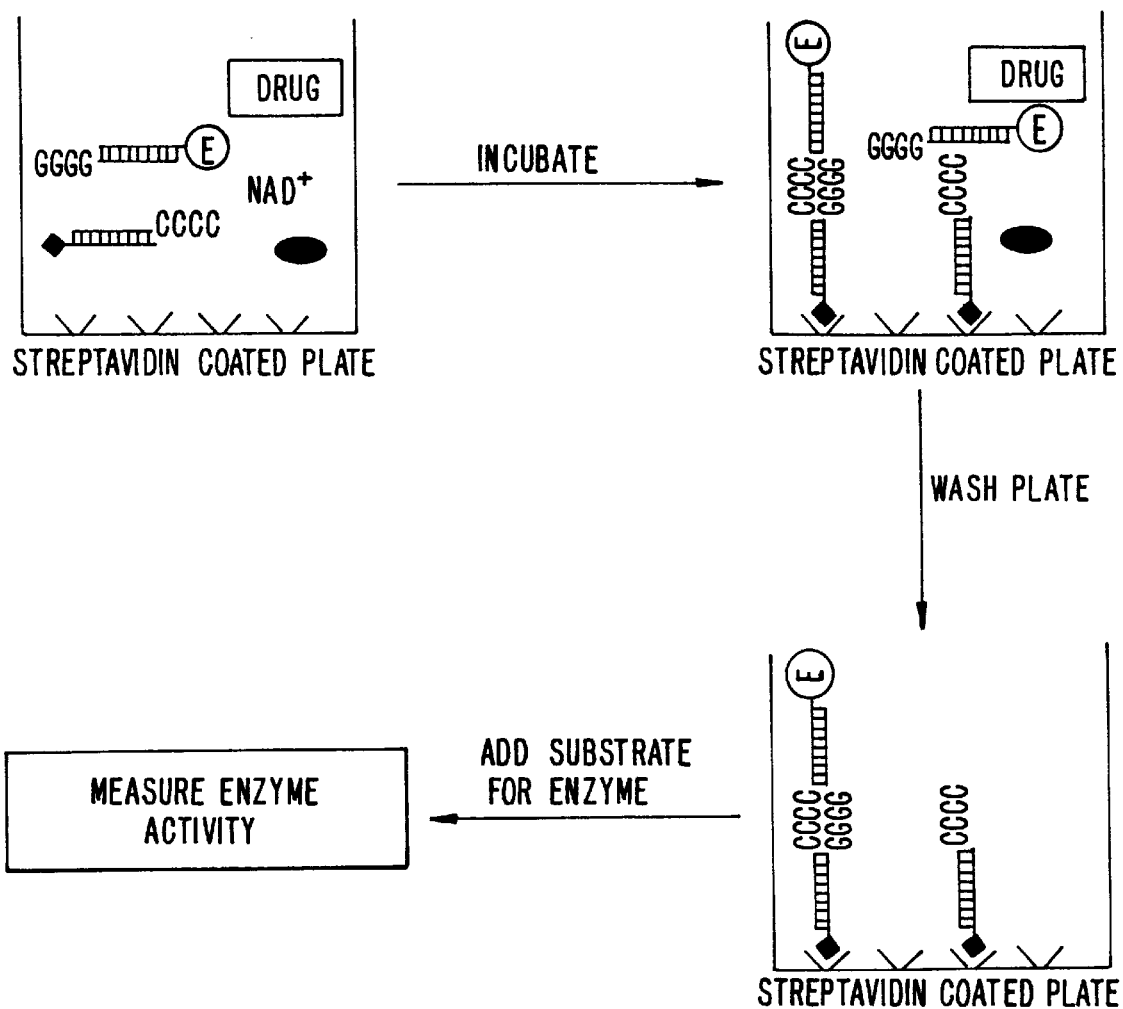
FIG. 2 is a drawing of a solid phase assay of the invention utilizing an enzymatic label.

FIG. 2 depicts a second preferred solid-phase assay format. In this embodiment, a DNA ligase is incubated in a ligation mixture comprising a tagged DNA comprising a biotin tag, a labeling DNA comprising an enzymatic label (e.g., an enzyme which catalyzes a colorimetric or luminescent reaction, such as a peroxidase), and appropriate buffers and co-factors (e.g., $NAD^{30}$, ATP or the like). The tagged DNA and the labeling DNA have complementary nucleic acid overhangs. Hybridization of the tagged DNA and the labeling DNA places a phosphate donor site on the labeling DNA into proximity of a phosphate acceptor site on the tagged DNA. The ligase enzyme catalyses chemical ligation of the tagged DNA to the labeling DNA. The ligation mixture is incubated in the presence of a solid substrate which binds to the biotin tag, such as a streptavidin or neutravidin coated plate. Following incubation, the solid substrate is washed, removing any unligated labeling DNA. The label is then quantitated, thereby determining how much of the labeling DNA is ligated to the tagged DNA. The activity of a ligase modulator ("DRUG" in FIG. 2) is measured by adding the modulator to the ligation mixture and measuring the resulting increase or decrease in label bound to the solid substrate.

It will be appreciated that ligation can be inhibited or facilitated by the addition of a nucleic acid modulator ("DRUG" in the figure) to the ligation mixture. Similarly, a modulator can simply increase or decrease the specificity of the ligase enzyme, as measured by comparison of the ligation rate on different substrates (DNA, RNA, different sequences, etc.) in the presence or absence of the modulator. Accordingly, a difference in the amount of label bound to the solid support following incubation with the modulator is indicative of ligase modulation activity. A decrease in the amount of label indicates that a compound inhibits ligation; similarly, a relative increase in the amount of bound label results from addition of a modulator which increases ligation activity.

Liquid Phase Assays

The liquid phase assays of the invention provide methods of measuring the activity of nucleic acid ligase in the presence of a potential ligase activity modulator. In the methods, a test ligation mixture including the nucleic acid ligase and nucleic acids to be ligated is incubated in the liquid phase.

Typically, the nucleic acids to be ligated are a first nucleic acid having a first label and a second nucleic acid optionally having a second label. The ligation mixture also includes a ligase activity modulator.

Alter incubation, the presence or absence of a detectable label emission is detected. The detected emission can be any of: an emission by the first label, an emission by the second label, and an emission resulting from a combination of the first and second label. In this assay, the presence or absence of the detectable emission indicates whether the first and second nucleic acid are ligated. Examples of the liquid phase assays are described in FIGS. 3 and 4, as discussed more fully below.

Labels

Moist typically in the liquid phase assays of the invention, the first and second label interact when in proximity (e.g., due to resonance transfer), and the relative proximity of the first and second labels is determined by measuring a change in the intrinsic fluorescence of the first or second label. Commonly, the emission of the first label is quenched by proximity of the second label.

Many appropriate interactive labels are known. For example, fluorescent labels, dyes, enzymatic labels, and antibody labels are all appropriate. Examples of preferred interactive fluorescent label pairs include terbium chelate and TRITC (tetrarhodamine isothiocyanate), europium cryptate and Allophycocyanin and many others known to one of skill. Similarly, two calorimetric labels can result in combinations which yield a third color, e.g., a blue emission in proximity to a yellow emission provides an observed green emission.

With regard to preferred fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of labels occurs. Fluorescent resonance energy transfer (FRET) is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals* Published by Molecular Probes, Inc., Eugene, Oreg. e.g., at chapter 13).

The Forster radius ($R_o$) is the distance between fluorescent pairs at which energy transfer is 50% efficient (i.e., at which 50% of excited donors are deactivated by FRET. The magnitude of $R_o$ is dependent on the spectral properties of donor and acceptor dyes:

$$R_o = [(8.8 \times 10^{23})(K^2)(n^{-4})(QY_D)(J)(\lambda)]^{1/6} \text{ Å}$$

where:

$K^2$=dipole orientation range factor (range 0 to 4, $K^2=\frac{2}{3}$ for randomly oriented donors and acceptors);

$QY_D$=fluorescence quantum yield of the donor in the absence of the acceptor;

n=refractive index; and, $J(\lambda)$=spectral overlap integral=$\int \epsilon_A(\lambda) \cdot F_D \lambda \cdot \lambda^4 d\lambda \text{cm}^3 \text{M}^{-1}$, Where $\epsilon_A$=extinction coefficient of acceptor and $F_D$=Fluorescence emission intensity of donor as a fraction of total integrated intensity.

Some typical $R_o$ are listed for typical donor-acceptor pairs:

| Donor | Acceptor | $R_0$(Å) |
| --- | --- | --- |
| Fluorescein | tetramethylrhodamine | 55 |
| IAEDANS | fluorescein | 46 |
| Fluorescein | Fluorescein | 44 |
| BODIPY | BODIPY | 57 |
| EDANS | DABCYL | 33 |

An extensive compilation of $R_o$ values are found in the literature; see, Haugland (1996) *Handbook of Fluorescent Probes and Research Chemicals* Published by Molecular Probes, Inc., Eugene, Oreg. at page 46 and the references cited therein.

In most uses, the donor and acceptor dyes are different, in which case FRET can be detected by the appearance of sensitized fluorescence of the acceptor or by quenching of the donor fluorescence. When the donor and acceptor are the same, FRET is detected by the resulting fluorescence depolarization.

In addition to quenching between fluorophores, individual fluorophores are also quenched by nitroxide-labeled molecules such as fatty acids. Spin labels such as nitroxides are also useful in the liquid phase assays of the invention.

Hybridization and Resolution

In the liquid phase methods of the invention, a first nucleic acid species is ligated to a second nucleic acid species in solution. Any unligated first and second nucleic acids are separated by heating the solution sufficiently to dissociate the first and second nucleic acid.

To facilitate ligation, the first and second nucleic acids typically comprise single-stranded complementary regions. As discussed above, this causes the nucleic acids to be located in close proximity for the ligation reaction. Following the ligation reaction, any unligated nucleic acids can be separated by heating the reaction mixture above the melting point of the complementary regions. The general considerations for determining melting point are discussed above. As an approximation, G-C base pairs in a duplex are estimated to contribute about 3° C. to the $T_m$, while A-T base pairs are estimated to contribute about 2° C., up to a theoretical maximum of about 80–100° C. However, more sophisticated models of $T_M$ and $T_d$ are available and appropriate in which G-C stacking interactions, solvent effects, the desired assay temperature and the like are taken into account.

For the assays of the present invention, the nucleic acid substrate is conveniently designed such that the labeled donor oligonucleotide does not form a stable hybrid with the plate-immobilized oligonucleotide at room temperature (22° C.) under the conditions of the assay. Prior to initiation of the assay, which is typically performed at room temperature, the nucleic acid substrate (formed by prior annealing of the composite oligonucleotides) is maintained at temperature significantly below room temperature (e.g., at 0° C. on ice). Hence during the course of the assay, labeled donor oligonucleotide which remains unligated dissociates from the plate-immobilized oligonucleotide and is removed from the reaction vessel (prior to the product detection phase of the assay) during the washing step. However, it will be appreciated that nucleic acids can be designed with much higher melting temperatures, as heat inactivation of the ligase is not an issue during heating (as the heating step occurs after the ligation step in the assay).

In a typical arrangement, similar to the solid phase assays described above, the first nucleic acid can include a first single-stranded overhang, with the second nucleic acid having a complementary single-stranded region which hybridizes to the first single-stranded overhang. Heating the ligation mixture destabilizes and releases unligated first and second nucleic acids.

In one preferred arrangement, the first nucleic acid has a template strand and a phosphate donor strand. The template strand overhangs the phosphate donor strand, providing a single stranded template overhang. The second nucleic acid has a single stranded region complementary to the overhang. Incubating the nucleic acid ligase, the first nucleic acid and the second nucleic acid in an absence of the ligase modulator (e.g., in a control or calibration reaction) results in ligation of the first and second nucleic acids. Sizes for the template strand, phosphate donor strand and second nucleic acid are similar to those discussed above for the template strand, phosphate donor strand and labeling nucleic acid for the solid phase assays, with one additional consideration. The first and second labels are spaced such that, upon ligation of the first and second nucleic acid, they are able to interact. This can be easily determined empirically for any combination of label pairs, by ligating the nucleic acids in the absence of a ligation modifier, using progressively longer distances between labels (i.e., by increasing the number of nucleotides between the labels), and monitoring the resulting changes in emission properties. As noted above, the literature provides $R_o$ for a large number of label pairs. Typically, the first and second nucleic acids will be between about 8 and about 40 nucleotides in length, with the first or second nucleic acid being at least about 10 nucleotides in length. However, depending on the placement of the labels, the nuclei, acids can be essentially any length.

The liquid phase assays of the invention are performed in essentially any liquid phase containers designed for high throughput screening. Most commonly, the ligation mixture is incubated in a well on a microtiter dish (many dish formats are known, e.g., 96 well, 384 well, etc).

Model Liquid Phase Assays

The liquid phase assays of the invention are further illustrated by consideration of the attached figures. These assays are provided by way of illustration and not by way of limitation; one of skill will recognize a variety of substitutions that can be made upon complete review of this disclosure.

FIG. 3 depicts a preferred time resolved liquid phase assay. A first DNA having a first label and a second DNA having a second label are hybridized in solution in the presence of a nucleic acid ligase. The nucleic acids have complementary single stranded overhangs. Hybridization of the first and second nucleic acids places a phosphate donor nucleotide in proximity to a phosphate acceptor nucleotide, and the ligase catalyzes chemical coupling of the first and second nucleic acids at this site. The first label is quenched by the second label. In this example, an exemplar first label is a Terbium chelate ("F") and exemplar second labels ("Q") include tetramethylrhodamine and nitroxide spin labels. Where a Tetramethylrhodamine is the second label, quenching of the first label is observed when the second label is up to about 10 nm (about 29 nucleotides) away. Where the second label is a nitroxide spin label, effective quenching is observed when the first and second labels are spaced up to about 2 nm (6 nucleotides) apart.

A second preferred time resolved liquid phase embodiment is described in FIG. 4. In this embodiment, a first nucleic acid having a template strand and a phosphate donor strand is hybridized to a second nucleic acid having a single-stranded region complementary to a portion of the template strand. The template strand is attached, covalently or non-covalently, to a label ("F"). The second nucleic acrid is attached, covalently or non-covalently, to a label which is modified by proximity to the first label, and/or which modifies the emission of a proximal first label. In this embodiment, example first labels include Terbium chelate and Europium Cryptate. Example second labels include TRITC and Allophycocyanin.

The nucleic acids are incubated with a ligase and appropriate buffers and co-factors for ligation. The action of the ligase covalently links the phosphate donor strand and the second nucleic acid. The mixture is then heated to a temperature higher than the melting temperature for the nucleic acid duplex formed between the template strand and the second nucleic acid, but lower than the melting temperature of the duplex formed between the template strand and a nucleic acid resulting from ligation of the phosphate donor strand and the second nucleic acid. Typically, the nucleic acids are selected so that hybridization occurs on ice, and heating is to room temperature. However, a wide variety of temperature combinations can be substituted.

Ligation is then monitored by measuring label emission (s). Where the second nuclei acid is ligated to the phosphate donor strand, the first and second labels are placed in proximity, yielding emission characteristics which differ from the first or second label alone. In one illustrated embodiment, the first and second labels are fluorescent and fluorescence resonance energy transfer yields a fluorescent emission different than either the first or second label alone.

The activity of a modulator is determined by adding the modulator prior to or during incubation of the first and second nucleic acid with the ligase and monitoring the resulting change in label emission relative to a control or base-line ligation reaction performed in the absence of the modulator.

Compositions, Kits and Integrated Systems

The invention provides compositions, kits and integrated systems for practicing the assays described herein. For example, an assay composition having a nucleic acid ligase enzyme, a tagged nucleic acid molecule comprising a tag, a nucleic acid ligase activity modulator and a labeled nucleic acid molecule is provided by the present invention. As discussed above regarding solid phase assays, the tagged nucleic acid molecule is typically partially complementary to the labeled nucleic acid molecule. The tagged nucleic acid can include a template strand and a phosphate donor strand in the arrangements described above. Typically, in the solid phase assays, the tag binds to a tag-binding molecule fixed to a solid substrate, thereby immobilizing the tagged nucleic acid on the solid substrate. Example tags include biotin, antibodies and the like as discussed above.

Similarly, a liquid phase assay composition includes a nucleic acid ligase enzyme, a first nucleic acid molecule having a first label, a second nucleic acid molecule having a second label, a nucleic acid ligase activity modulator and, a labeled nucleic acid molecule. Typically, the first nucleic acid molecule is partially complementary to the second nucleic acid molecule. As discussed in detail above, the first label is typically quenched by the second label (or the second quenched by the first) when the first and second labels are in close proximity. In the example noted above, the first label is quenched by the second label when the first label is within about 10 nm of the second label.

The invention also provides kits for practicing the methods noted above the kits can include any of the compositions noted above, and optionally further include additional components such as instructions to practice a high-throughput method of screening for a ligase inhibitor, one or more containers or compartments (e.g., to hold ligase, nucleic acids, or the like), a control nucleic acid ligase activity modulator, a robotic armature for mixing kit components or the like.

The invention also provides integrated systems for high-throughput screening of potential ligase modulators for an effect on a ligase. The systems typically include a robotic armature which transfers fluid from a source to a destination, a controller which controls the robotic armature, a label detector, a data storage until which records label detection, and an assay component such as a microtiter dish comprising a well having a ligation mixture or a substrate comprising a fixed nucleic acid having a label detected by the label detector. In the later embodiment, the fixed nucleic acid includes a tag which is bound to the solid support and the label is covalently attached to the fixed nucleic acid by the action of a ligase enzyme.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) Pipetting station can be used to transfer parallel samples to 96 well microtiter plates to set up several parallel simultaneous ligation reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel ×86 or pentium chip- compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

The following examples are provided by way of illustration only and not by way of limitation. Those of skill will readily recognize a variety of noncritical parameters which are changed or modified to yield essentially similar results.

1. *E. coli* DNA LIGASE ASSAY

Ligase:

*E. coli* DNA Ligase, New England Biolabs, Cat #205L ($150 for 1,000U).

Concentration range in the assay is 10 to 50 pM.

Antibody:

Anti-Fluorescein-POD, Boehringer Mannheim, Cat #1 426 346 ($154 for 150U).

Make up to 1 ml with water.

DNA Mix:

The assay requires 3 different oligos used in an annealed mixture.

1). Template: Biotin-5'-GCC ACT ACG AAG GCA CCA ACC TTT TTT T

2.) PO$_4$ oligo: PO$_4$-5'-TGG TGC CTT CGT AGT GGC

3.) Fluorescein oligo: Fluorescein-5'-AAA AAA AGG T

Add 25 μl of 1) and 2) oligo (20 pmol/μl) +50 μl 10×Annealing buffer +375 μl water. Heat for 2 minutes at 100° C., add 25 μL of 3), and followed by incubation for 30 min at 37° C. and then for >30 min on ice. Concentration of the DNA in this mix is thus 1 pmol/μl. Concentration range used in the assay is 0.5 to 1 nM (the assay has also been performed at 0.75–2 nM).

Assay buffer (10×):

300 mM Tris, pH8

500 μg/ml BSA 40 mM MgCl$_2$

Antibody dilution buffer:

10 mM Hepes, pH 7.9

50 mM NaCl 1 mM EDTA 0.1% NP40

0.1 mg/ml BSA

ASSAY PROTOCOL:

Make 1× buffer with 1 mM DTT and 32.5 gM NAD$^{30}$. Note that NAD$^{30}$ (Sigma, Cat #4020, $83/gm) is unstable at room temp. Make a 100×stock, aliquot and freeze at −20° C.

1 Add 80 μl of above buffer containing DNA to wells in a Neutravidin, or streptavidin coated plate.

2) Add 10 μl compound/DMSO.

3) Add 10 μl Ligase (in buffer minus NAD$^{30}$); let reaction proceed (50 min).

4) Wash 4× with water.

5) Add 100 μl antibody (1/10,000 in antibody dilution buffer), stand for 50 min.

6) Wash 4× with water.

7) Add substrate (SuperSignal LBA, 1 to 5 dilution in water) and read.

Results

The results of various *E. coli* ligase assays are provided in FIGS. 5a–7.

Figure 5A:
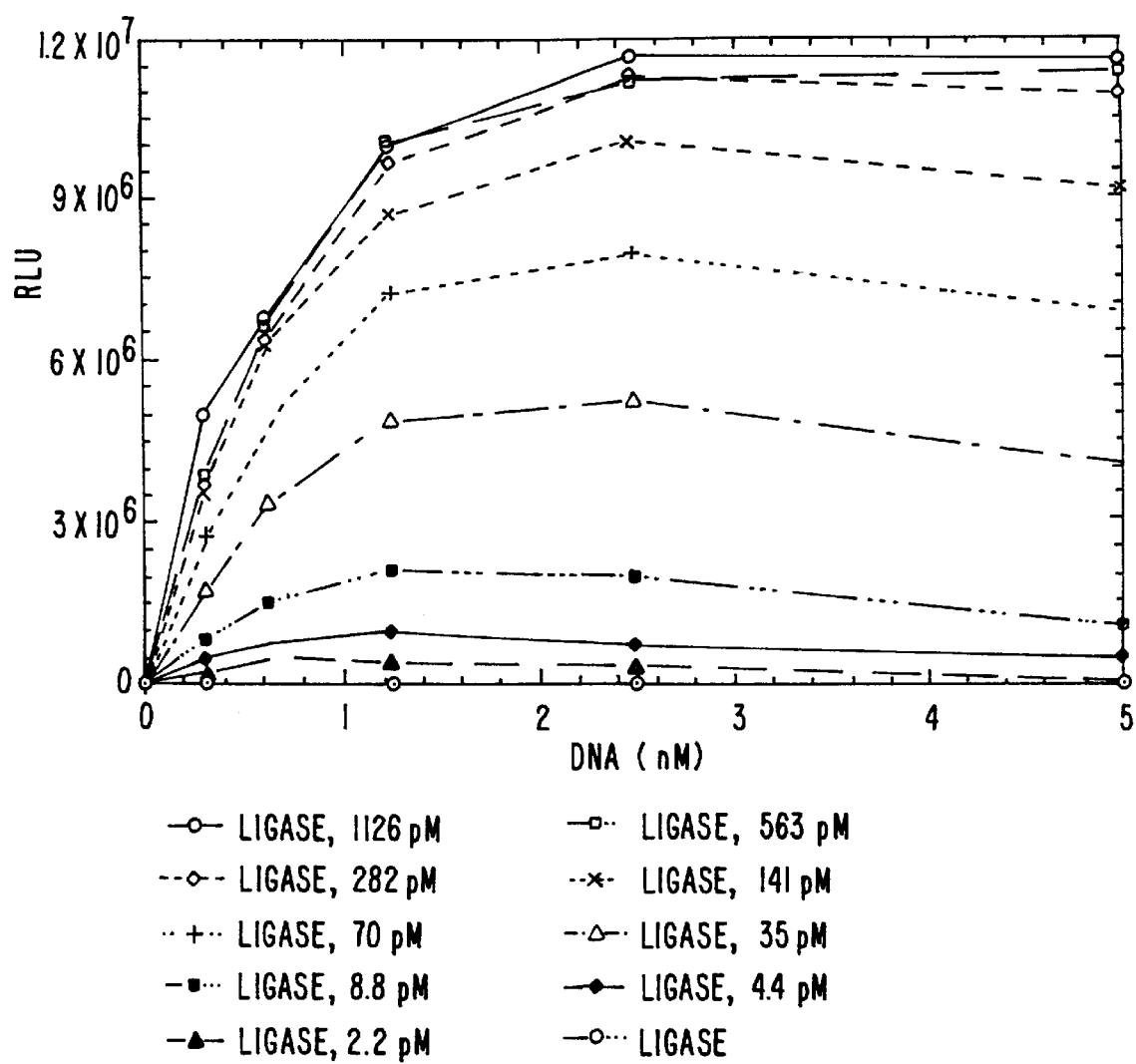
FIGS. 5A & 5B are graphical representations of DNA ligase assay development data.

FIG. 5a shows the optimization of the substrate (template) to enzyme ratio for use in the assay described above and, e.g., in FIG. 1. *Escheria coli* DNA Ligase from New England Biolabs was used as discussed above. A neutravidin coated plate from Pierce was used in the assay. Buffers, incubation times and product detection were as described above. The readout is from a luminometer; RLU=Relative Light Units.

Figure 5B:
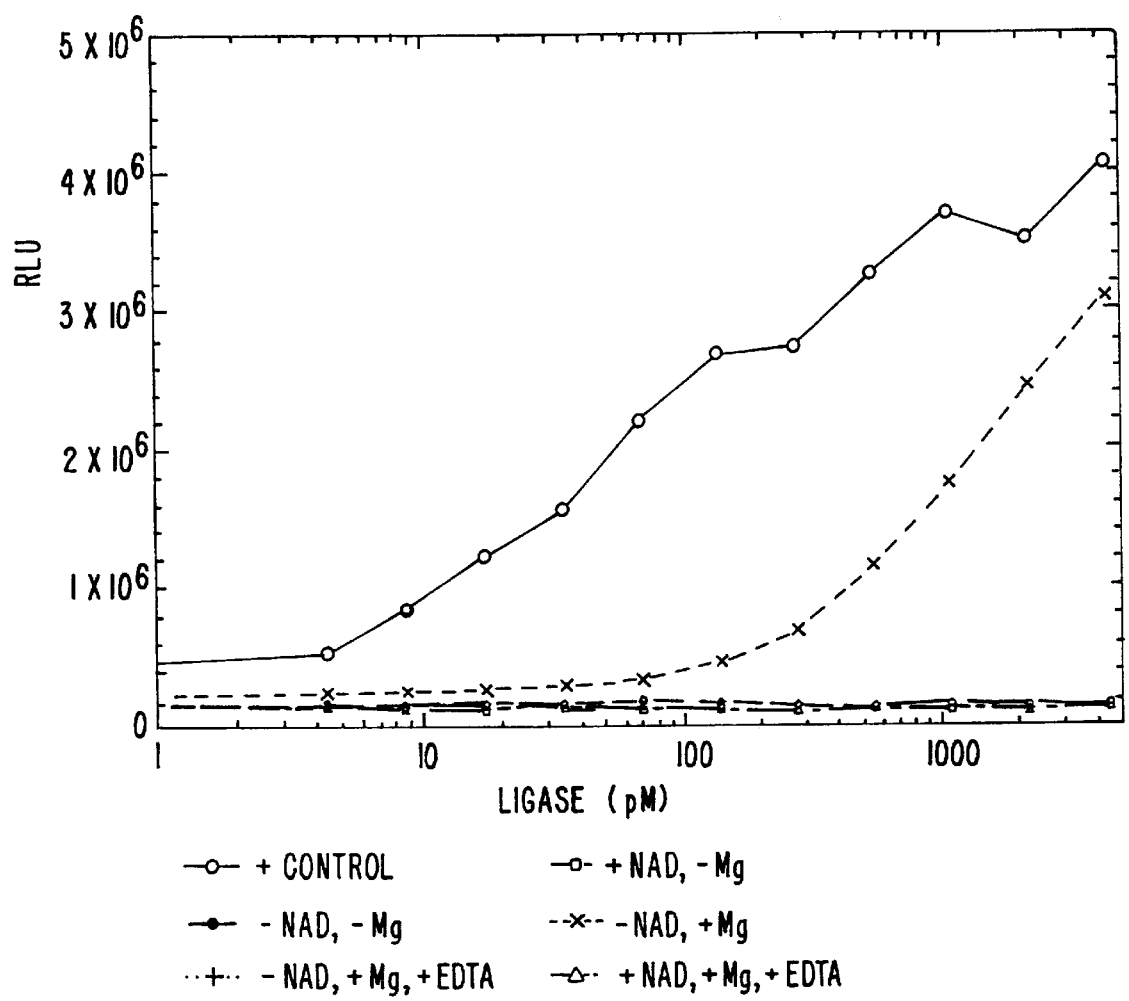

FIG. 5b shows representative data obtained during assay development showing the dependence of the reaction on Mg$^{+2}$ ions and NAD$^{30}$. Data was obtained using assay conditions essentially as described above and in FIG. 1. *Escheria coli* DNA Ligase from New England Biolabs was used as discussed above. Substrate concentration was 250 pM. A neutravidin coated plate from Pierce was used in the assay. Buffers, incubation times and product detection were as described above, except for the concentration of Mg$^{+2}$ and NAD$^{30}$ indicated in the figure. The readout is for a luminometer; RLU=Relative Light Units.

Figure 6A:
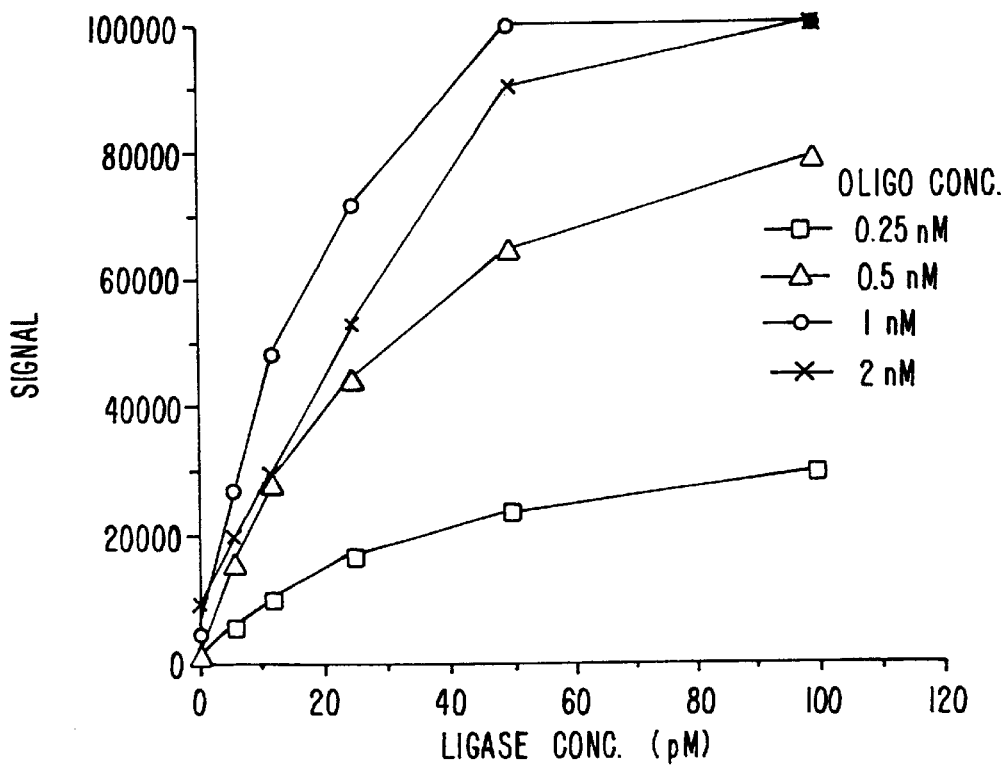
FIGS. 6A & 6B are graphical representations of DNA ligase assay development data using different forms of DNA ligase.

FIG. 6a shows representative data obtained during optimization of the substrate (template) to enzyme ratio for use in a robotic format of the assay. Data was obtained using assay conditions essentially as described above and in FIG. 1. *Escheria coli* DNA Ligase from New England Biolabs was used as discussed above. A neutravidin coated plate from Pierce was used in the assay. Buffers, incubation times and product detection were as described above, except that a wash buffer of 0.1% NP-40 detergent in deionized water was used. The readout is from a luminometer; "signal" is in Relative Light Units.

Figure 6B:
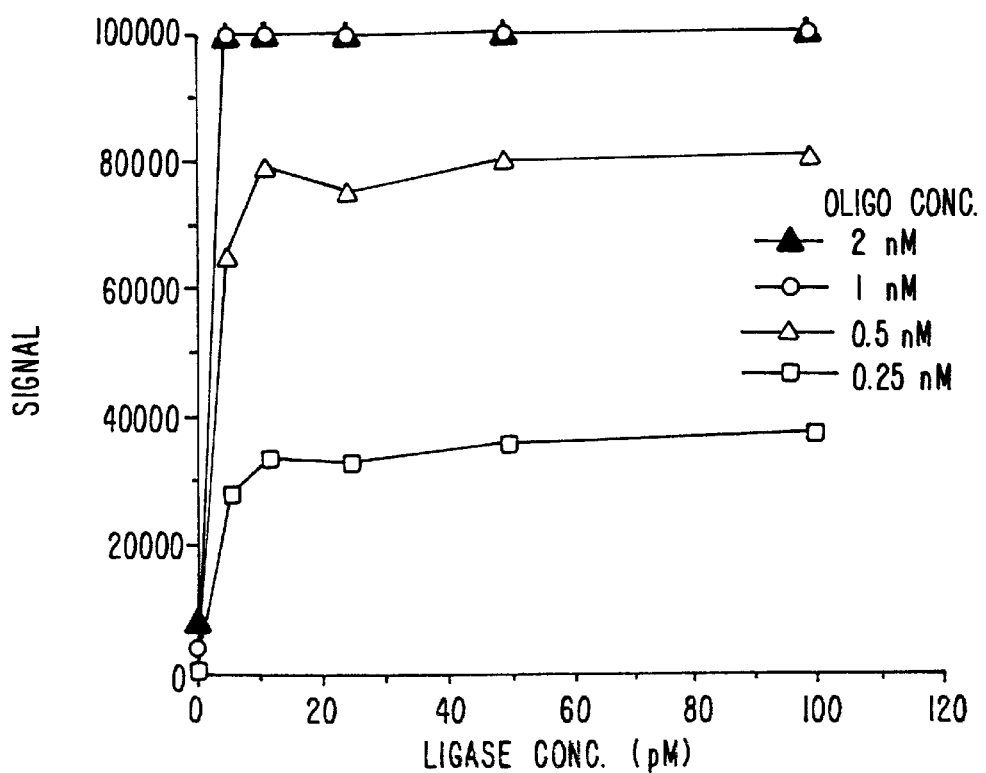

FIG. 6b shows representative data obtained during optimization of the substrate (template) to enzyme ratio for use in a robotic format of the assay. The ligase enzyme in this assay was a recombinant form of *Escheria coli* DNA Ligase which bears a polyhistadine affinity tag at its amino terminus. A neutravidin coated plate from Pierce was used in the assay. Buffers, incubation times and product detection were as described above, except that a wash buffer of 0.1% NP-40 detergent in deionized water was used. The readout is from a luminometer; "signal" is in Relative Light Units.

FIG. 7 shows representative data obtained from fully automated robotic assays. Data obtained from robotic assays was obtained as described above and as depicted, e.g., in FIG. 1. Control reactions in which no enzyme is added to the reaction are included in the first row of each plate (wells A1–H1). Control reactions in which only DMSO (final concentration of 10%) is added to the reaction are included in the last row of each plate (wells A12-H12). Other wells contain chemical compounds which are dissolved in 100% DMSO and are added to the reaction such that DMSO contributes 10% to the final volume. *Escheria coli* DNA Ligase from New England Biolabs was used as discussed above at a concentration of 50 pM in plate rows 2–12. A concentration of substrate of 330 pM was used in all wells. A neutravidin coated plate from Pierce was used in the assay. Buffers, incubation times and product detection were as described above, using a wash buffer of 0.1% NP-40 detergent in deionized water. The readout is from a luminometer; readout is in Relative Light Units.

Accordingly, the disclosures and descriptions herein are intended to be illustrative, bat not limiting, of the scope of the invention which is set forth in the following claims. All patents and publications cited herein are incorporated in their entirety for all purposes, as though each were individually indicated to be incorporated by reference.

What is claimed is:

1. A method of measuring the activity of a nucleic acid ligase in the presence of a potential nucleic acid ligase activity modulator, comprising:

incubating a test ligation mixture comprising: a nucleic acid ligase; a tagged nucleic acid comprising template strand which comprises a tag; a labeling nucleic acid comprising a primary label, wherein the labeling nucleic acid is fully complementary to at least part of the template strand; a phosphate donor or a phosphate acceptor strand that is fully complementary to at least part of the template strand; and a potential activity modulator;

binding the tag to a solid support, thereby binding the tagged nucleic acid to the solid support; and, determining whether the labeling nucleic acid is ligated to the phosphate donor or the phosphate acceptor strand and forms a duplex with the tagged nucleic acid by detecting the presence or absence of the labeling nucleic acid on the solid support, thereby determining the activity of the ligase in the test mixture.

2. The method of claim 1, wherein the tagged nucleic acid is partially double stranded, comprising the template strand and the phosphate donor strand, the template strand overhanging the phosphate donor strand, thereby providing a single-stranded template overhang, wherein the labeling nucleic acid comprises a single stranded region complementary to the overhang, and wherein incubating a control ligation mixture comprising the nucleic acid ligase, the tagged nucleic acid, and the labeling nucleic acid, in the absence of the potential activity modulator, results in ligation of the tagged nucleic acid to the labeling nucleic acid.

3. The method of claim 2, wherein incubating a test ligation mixture comprising the potential activity modulator results in a lower rate of ligation between the tagged nucleic acid and the labeling nucleic acid than the control ligation mixture.

4. The method of claim 1, further comprising quantitating the amount of labeling nucleic acid bound to the solid support.

5. The method of claim 1, wherein the labeling nucleic acid is selected from the group consisting of: a single-stranded RNA, a double-stranded RNA, a single-stranded DNA, a double-stranded DNA, a double-stranded DNA-RNA hybrid, an RNA analogue, and a DNA analogue, and wherein the tagged nucleic acid is selected from the group consisting of a double-stranded RNA, a double-stranded DNA, a double-stranded DNA-RNA hybrid, an RNA analogue, and a DNA analogue.

6. The method of claim 1, wherein the nucleic acid ligase is selected from the group consisting of: an $NAD^{30}$-dependent nucleic acid ligase, an ATP-dependent nucleic acid ligase, and a nucleic acid ligase from a prokaryotic, eukaryotic, or viral source.

7. The method of claim 1, wherein the labeling nucleic acid is detected by binding a secondary label to the primary label and detecting the secondary label.

8. The method of claim 7, wherein the primary label and the secondary label are independently selected from the group consisting of: a radioactive label, a fluorophore, a dye, an enzyme, an enzyme substrate, and an antibody.

9. The method of claim 7, wherein the primary label comprises a fluorescein and the secondary label is a peroxidase-conjugated anti-fluorescein antibody.

10. The method of claim 1, wherein the labeling nucleic acid is detected by detecting the primary label.

11. The method of claim 1, wherein the solid support comprises a substrate coated with streptavidin or neutravidin and the tag comprises a biotin moiety.

12. The method of claim 1, wherein the tagged nucleic acid is immobilized on the solid support through an interaction selected from the group consisting of: non-covalent binding of a ligand to a ligand binding moiety, and covalent attachment of at least the template strand of the tagged nucleic acid to the solid support.

13. The method of claim 1, wherein the method further comprises the step of washing tinligated labeling nucleic acid from the solid support.

14. The method of claim 13, wherein unligated labeling nucleic acid hybridizes to the tagged nucleic acid during the step of incubating the test ligation mixture and wherein unligated labeling nucleic acid is released from the tagged nucleic acid during the step of washing the unligated labeling nucleic acid from the solid support.

15. The method of claim 1, wherein the labeling nucleic acid is between about 8 and about 20 nucleotides in length.

16. The method of claim 1, wherein the labeling nucleic acid is about 10 nucleotides in length.

17. The method of claim 1, wherein the tagged nucleic acid comprises a template strand at least about 28 nucleotides in length.

18. The method of claim 1, wherein the potential modulator is selected from the group consisting of: a ligase inhibitor, and a ligase activator.

19. A method of measuring the activity of nucleic acid ligase in the presence of a potential ligase activity modulator comprising:

incubating a test ligation mixture comprising the nucleic acid ligase; a first nucleic acid comprising a first label and a first single-stranded overhang; a second nucleic acid comprising a second label and a complementary second single-stranded region which hybridizes to the first single-stranded overhang and the ligase activity modulator; and, detecting, in a liquid phase, the presence or absence of a detectable emission selected from the group consisting of: an emission by the first label, an emission by the second label, and an emission resulting from a combination of the first and second label, wherein the presence or absence of the detectable emission indicates whether the first and second nucleic acid are ligated.

20. The method of claim 19, wherein the relative proximity of the first and second labels is determined by measuring a change in the intrinsic fluorescence of the first or second label.

21. The method of claim 19, wherein the emission of the first label is quenched by proximity of the second label.

22. The method of claim 19, further comprising heating the test ligation mixture.

23. The method of claim 19, wherein the first nucleic acid comprises a first single-stranded overhang, and wherein the second nucleic acid comprises a complementary single-stranded region which hybridizes to the first single-stranded overhang, wherein heating the ligation mixture destabilizes and releases unligated first and second nucleic acids.

24. The method of claim 23, wherein the ligation mixture is heated to room temperature, thereby destabilizing and releasing unligated first and second nucleic acids.

25. The method of claim 19, wherein the first nucleic acid comprises a template strand and a phosphate donor strand, the template strand overhanging the phosphate donor strand, thereby providing a single-stranded template overhang, wherein the second nucleic acid comprises a single stranded region complementary to the overhang, and wherein incubating the nucleic acid ligase, the first nucleic acid and the second nucleic acid in an absence of the ligase modulator results in ligation of the first and second nucleic acids.

26. The method of claim 22, wherein heating the ligation mixture dissociates unligated first and second nucleic acids.

27. The method of claim 19, wherein the second nucleic acid comprises a second label.

28. The method of claim 19, wherein the first and second labels are independently selected from the group consisting of: a fluorescent label, a dye, an enzymatic label, and an antibody label.

29. The method of claim 20, wherein the first label is selected from the group consisting of: terbium chelate, and europium cryptate; and wherein the second label is selected from the group consisting of: TRITC, and Allophycocyanin.

30. The method of claim 19, wherein the first and second nucleic acids are between about 8 and about 40 nucleotides in length.

31. The method of claim 19, wherein the first or second nucleic acid is at least about 10 nucleotides in length.

32. The method of claim 19, wherein the nucleic acid ligase is selected from the group consisting of: an $NAD^{30}$-dependent nucleic acid ligase, an ATP-dependent nucleic acid ligase, and a nucleic acid ligase from a prokaryotic, eukaryotic or viral source.

33. The method of claim 19, wherein the test ligation mixture is incubated in the liquid phase in well on a microtiter dish.

34. A composition comprising: a nucleic acid ligase enzyme; a tagged nucleic acid comprising a template strand which comprises a tag; a nucleic acid ligase activity modulator; a phosphate donor or a phosphate acceptor strand that is fully complementary to at least part of the template strand; and, a labeled nucleic acid, wherein the tagged nucleic acid is fully complementary to at least part of the labeled nucleic acid molecule.

35. The composition of claim 34, wherein the tag binds to a tag-binding molecule fixed to a solid substrate, thereby immobilizing the tagged nucleic acid on the solid substrate.

36. The composition of claim 34, wherein the tag is a biotin molecule.

37. A composition comprising a nucleic acid ligase enzyme; a first nucleic acid comprising a first label; a second nucleic acid comprising a second label; and a nucleic acid ligase activity modulator, wherein the first nucleic acid is fully complementary to at least part of the second nucleic acid and wherein the first label is quenched by the second label when the first and second labels are in close proximity.

38. The composition of claim 37, wherein the first label is quenched by the second label when the first label is within about 10 nm of the second label.

39. The composition of claim 37, wherein the first and second labels are fluorescent labels.

40. The composition of claim 37, wherein the first label is selected from the group consisting of: terbium chelate, and europium cryptate; and the second label is selected from the group consisting of: TRITC, and Allophycocyanin.

41. The composition of claim 37, wherein the relative proximity of the first and second labels is determined by measuring a change in the intrinsic fluorescence of the first or second label.

42. A kit comprising a nucleic acid ligase enzyme; a first nucleic acid having a first label; and a second nucleic acid molecule having a second label, wherein the first nucleic acid is fully complementary to at least part of the second nucleic acid and wherein the first label is quenched by the second label when the first and second labels are in close proximity, a control nucleic acid ligase activity modulator the kit further comprising one or more component selected from the group consisting of: instructions to practice a high-throughput method of screening for a ligase inhibitor, one or more containers or compartments, and a robotic armature for mixing kit components.

43. An integrated system for high-throughput screening of potential ligase modulators for an effect on a ligase, comprising: a robotic armature which transfers fluid from a source to a destination; a controller which controls the robotic armature; a label detector, a data storage unit which records label detection; and an assay component selected from the group consisting of:

a microtiter dish comprising a well having a nucleic acid ligase enzyme; a control nucleic acid ligase activity modulator; a first nucleic acid having a first label; and a second nucleic acid having a second label, wherein the first nucleic acid is fully complementary to at least part of the second nucleic acid and wherein the first label is quenched by the second label when the first and second labels are in close proximity, which quenching is detected by the label detector; and, a substrate comprising a fixed nucleic acid having a label detected by the label detector, wherein the fixed nucleic acid comprises a tag which is bound to the solid support and wherein the label is covalently attached to the fixed nucleic acid by the action of a ligase enzyme and a control nucleic acid ligase modulator.

44. The method of claim 1, wherein the tagged nucleic acid is partially double stranded, comprising the template strand and the phosphate acceptor strand, the template strand overhanging the phosphate acceptor strand, thereby providing a single-stranded template overhang, wherein the labeling nucleic acid comprises a phosphate donor and a single stranded region complementary to the overhang, and further comprising the step of incubating a control ligation mixture comprising the nucleic acid ligase, the tagged nucleic acid, and the labeling nucleic acid, in the absence of the potential activity modulator, thereby resulting in ligation of the tagged nucleic acid to the labeling nucleic acid in the control ligation mixture.

45. The method of claim 19, wherein the first nucleic acid comprises a template strand and a phosphate acceptor strand, the template strand overhanging the phosphate acceptor strand, thereby providing a single-stranded template overhang, wherein the second nucleic acid comprises a phosphate donor and a single stranded region complementary to the overhang, and further comprising the step of incubating a control reaction mixture comprising the nucleic acid ligase, the first nucleic acid and the second nucleic acid in an absence of the ligase modulator, thereby resulting in ligation of the first and second nucleic acids in the control reaction mixture.

46. A method of measuring the activity of nucleic acid ligase in the presence, of a potential ligase activity modulator comprising:

incubating a test ligation mixture comprising the nucleic acid ligase; a first nucleic acid comprising a first label; a second nucleic acid comprising a second label; and the ligase activity modulator, wherein the first nucleic acid is labeled at a 5' end of a strand and the second nucleic acid is labeled at a 3' end of a strand so that upon ligation the first and second labels are on a same end of a duplex nucleic acid; and, detecting, in a liquid phase, the presence or absence of a detectable emission selected from the group consisting of: an emission by the first label, an emission by the second label, and from a combination of the first and second label, wherein the presence or absence of the detectable emission from a combination of the first and second label indicates whether the first and second nucleic acid are ligated.

47. The method of claim 46, wherein the first nucleic acid comprises a template strand labeled at the 3' end and a phosphate donor strand, the template strand overhanging the phosphate donor strand, thereby providing a single-stranded template overhang, wherein the second nucleic acid comprises a phosphate acceptor strand labeled at the 5' end and a single stranded region complementary to the overhang, and wherein incubating the nucleic acid ligase, the first nucleic acid and the second nucleic acid in an absence of the ligase modulator results in ligation of the first and second nucleic acids.

* * * * *

UNITED STATES PATENT AND TRADEMARK OFFICE
CERTIFICATE OF CORRECTION

PATENT NO.    : 6,153,384
DATED         : November 28, 2000
INVENTOR(S)   : Lynch et al.

It is certified that error appears in the above-identified patent and that said Letters Patent is hereby corrected as shown below:

Column 19,
Line 64, delete "NAD $^{30}$" and substitute therefor -- NAD$^+$ --;

Column 20,
Line 23, delete "tinligated" and substitute therefor -- unligated --;

Column 21,
Line 34, delete "NAD $^{30}$" and substitute therefor -- NAD$^+$ --; and Column 22,
Line 12, after "modulator", insert -- , --.

Signed and Sealed this

Fourteenth Day of January, 2003

JAMES E. ROGAN
*Director of the United States Patent and Trademark Office*